US007951575B2

(12) United States Patent
Bruessow et al.

(10) Patent No.: US 7,951,575 B2
(45) Date of Patent: *May 31, 2011

(54) ISOLATED PHAGES AND THEIR USE IN FOOD OR PET FOOD PRODUCTS

(75) Inventors: Harald Bruessow, La Tour-de-Peliz (CH); Sandra Chennoufi, Epalinges (CH); Josette Sidoti, Paudex (CH); Anne Bruttin, Lausanne (CH)

(73) Assignee: Nestec S.A., Vevey (CH)

( * ) Notice: Subject to any disclaimer, the term of this patent is extended or adjusted under 35 U.S.C. 154(b) by 230 days.

This patent is subject to a terminal disclaimer.

(21) Appl. No.: 11/626,196

(22) Filed: Jan. 23, 2007

(65) Prior Publication Data

US 2007/0134207 A1 Jun. 14, 2007

Related U.S. Application Data

(63) Continuation of application No. 10/864,604, filed on Jun. 10, 2004, now Pat. No. 7,211,426, which is a continuation of application No. PCT/EP02/12184, filed on Oct. 30, 2002.

(30) Foreign Application Priority Data

Dec. 13, 2001 (EP) .................................. 01204879

(51) Int. Cl.
*C12N 7/00* (2006.01)
(52) U.S. Cl. .................................................. 435/235.1
(58) Field of Classification Search .................. None
See application file for complete search history.

(56) References Cited

U.S. PATENT DOCUMENTS

| | | | |
|---|---|---|---|
| 4,957,686 A | 9/1990 | Norris | |
| 5,688,501 A | 11/1997 | Merril et al. | |
| 5,952,033 A | 9/1999 | Anantharaman et al. | |
| 5,968,569 A | 10/1999 | Cavadini et al. | |
| 6,121,036 A | 9/2000 | Ghanbari et al. | |
| 6,461,608 B1 | 10/2002 | Averback et al. | |
| 6,699,701 B1 | 3/2004 | Sulakvelidze et al. | |
| 7,211,426 B2 * | 5/2007 | Bruessow et al. | 435/235.1 |
| 2001/0043917 A1 | 11/2001 | Merril et al. | |

FOREIGN PATENT DOCUMENTS

WO WO 98/47521 10/1998

OTHER PUBLICATIONS

Berchieri, A. Jr. et al., "The Activity in the Chicken Alimentary Tract of Bacteriophages Lytic for *Salmonella* Typhimurium," Research in Microbiology, vol. 142, No. 5, pp. 541-549 (1991).
Blattner, F.R. et al., "The Complete Genome Sequence of *Escherichia coli* K-12," Science, vol. 277, pp. 1453-1474 (1997).
Hayashi, T. et al., "Complete Genome Sequence of Enterohemorrhagic *Eschelichia coli* O157:H7 and Genomic Comparison With a Laboratory Strain K-12," DNA Research, vol. 8, pp. 11-22 (2001).
Perna, N.T. et al., "Genome Sequence of Enterohaemorrhagic *Escherichia coli* O157:H7," Nature, vol. 409, pp. 529-533 (2001).
Smith, H.W. et al., "Successful Treatment of Experimental *Escherichia coli* Infections in Mice Using Phage: Its General Superiority Over Antibiotics," J. Gen. Microbiol., vol. 128, pp. 307-318 (1982).
Smith, H.W. et al., "The Control of Experimental *Escherichia coli* Diarrhoea in Cavles by Means of Bacteriophages," J. Gen. Microbiol., vol. 133, No. 5, pp. 1111-1126 (1987).
XP002198638, Derwent Publications LTD. Abstract (1992).
Tetard et al. "Phylogeny of the Major Head and Tail Genes of the Wide-Ranging T4-Type Bacteriophages," Journal of Bacteriology, vol. 183, No. 1, pp. 358-366 (2001).
Karam et al., "Molecular Biology of Bacteriophage T4," ASM Press, pp. 4,494-501 (1994).
Yu et al., "Characterization of a Phage Specific to Hemorrhagic *Escherichia coli* O157:H7 and Disclosure of Variations in Host Outer Membrane Protein OMPC," Journal of Biomedical Science, vol. 5, No. 5, pp. 370-382 (1998).
Ronner et al., "Isolation and Characterization of a Coliphage Specific for *Escherichia coli* O157:H7," Journal of Food Protection, vol. 53, No. 11, pp. 944-947 (1990).
Goodridge et al., "Morphological, Host Range, and Genetic Characterization of Two Coliphages," Applied and Environmental Microbiology, vol. 69, No. 9, pp. 5364-5371 (2003).

\* cited by examiner

*Primary Examiner* — Vera Afremova
(74) *Attorney, Agent, or Firm* — K&L Gates LLP

(57) ABSTRACT

The present invention relates to phage isolates having a strong lytic activity against pathogenic Enterobacteriaceae such as *Escherichia coli* and/or *Salmonella* strains and their use in various human or pet food products for the treatment or prevention of bacterial diseases caused by pathogenic Enterobacteriaceae such as *Escherichia coli*, in particular for phage therapy of pediatric gastroenteritis, or *Salmonella* infection. It also relates to human or pet food products prepared thereof.

12 Claims, 5 Drawing Sheets

ISOLATED PHAGES AND THEIR USE IN FOOD OR PET FOOD PRODUCTS

CROSS-REFERENCE TO RELATED APPLICATIONS

Figure 1:
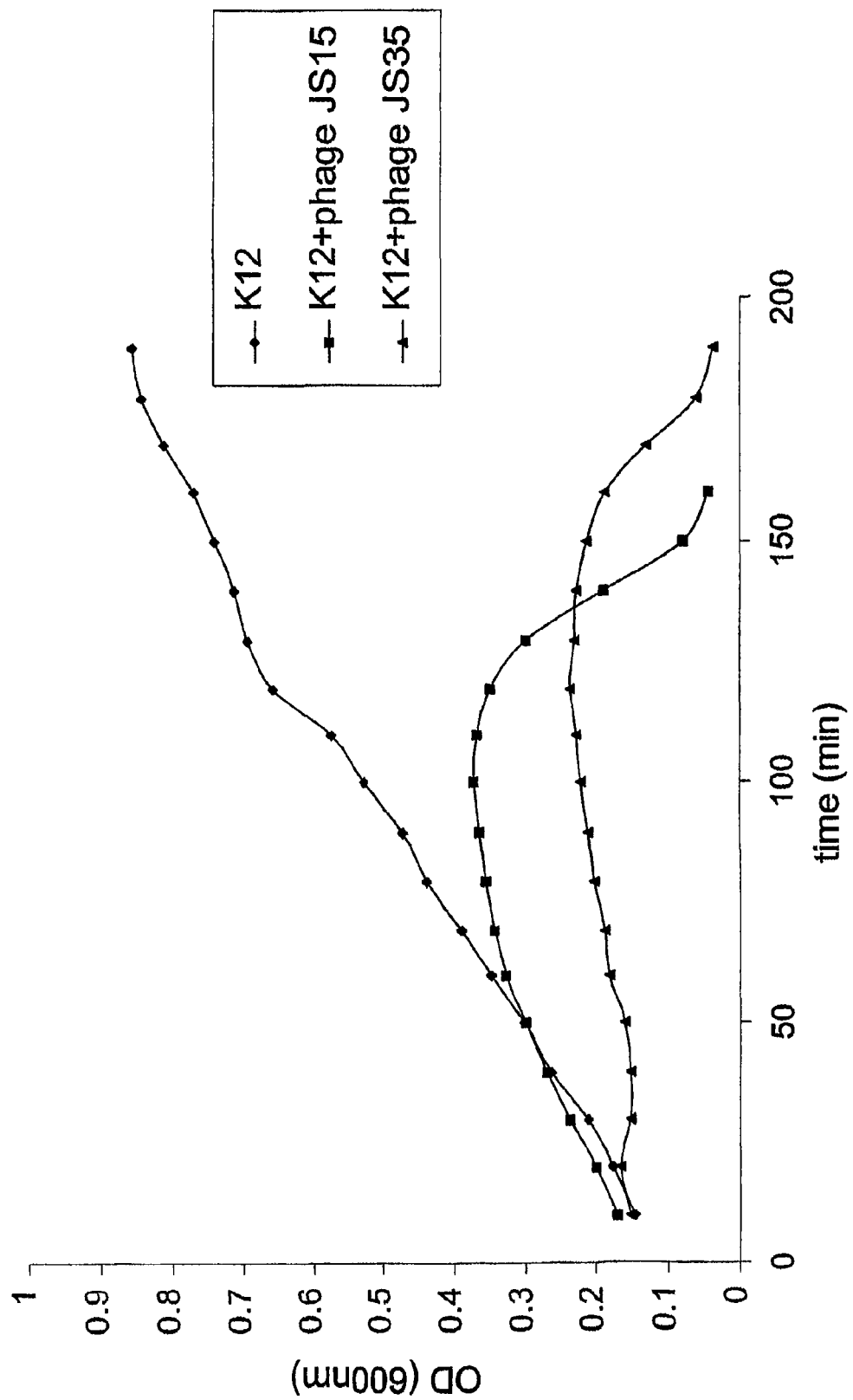

This application is a continuation of U.S. application Ser. No. 10/864,604 filed on Jun. 10, 2004, which is a continuation of International application no. PCT/EP02/12184, filed on Oct. 30, 2002, the entire contents of which are expressly incorporated herein by reference.

FIELD OF THE INVENTION

The present invention relates to phage isolates having a strong lytic activity against pathogenic Enterobacteriaceae such as *Escherichia coli* and *Salmonella* strains and their use in various human or pet food products for the treatment or prevention of bacterial diseases caused by pathogenic Enterobacteriaceae such as *Escherichia coli* or *Salmonella*, in particular for phage therapy of pediatric gastroenteritis. It also relates to human or pet food products prepared thereof.

BACKGROUND OF THE INVENTION

In the past, antibiotics have been used to treat various infections. The work of Selman Waksman in the introduction and production of Streptomycetes, and Dr. Fleming's discovery of penicillin, as well as the work of numerous others in the field of antibiotics, are well known. Over the years, there have been additions and chemical modifications to the "basic" antibiotics in attempts to make them more powerful, or to treat people allergic to these antibiotics.

However, as more antibiotics have been prescribed or used at an ever-increasing rate for a variety of illnesses, increasing numbers of bacteria have developed a resistance to antibiotics. Larger doses of stronger antibiotics are now being used to treat ever more resistant strains of bacteria. Consequently, multiple antibiotic resistant bacteria have been developed and some hospital-acquired infections with Gram-positive bacteria have already become untreatable. The use of more antibiotics and the number of bacteria showing resistance has led to increases in the amount of time that the antibiotics need to be used. Broad, non-specific antibiotics, some of which have detrimental effects on the patient, are now being used more frequently. Additionally, the number of people showing allergic reactions to antibiotics appears to be increasing.

Consequently, other efforts have been sought to first identify and then kill bacteria.

Attempts have been made to treat bacterial diseases with the use of bacteriophages. These are a heterogeneous group of viruses that infect bacteria that were first discovered in the early part of the 20th Century (d'Herelle, F., The bacteriophage. Its role in immunity, translated by Smith, G. H., Williams & Wilkins Co., Baltimore (1922)). Bacteriophages presently are widely used in scientific research, such as in molecular biology (e.g. as genetic vectors) and in medical diagnostics (e.g. phage typing of bacteria). Insofar as phages naturally infect and kill bacteria, it traditionally was suggested that they could be utilized in medical therapeutics, because bacteria are a major cause of disease.

Indeed, potential therapeutic uses of phage in experimental systems have been reported extensively in the literature.

For example, U.S. Pat. No. 5,688,501 (Merril, et al.) discloses a method for treating an infectious bacterial disease with lytic or non-lytic bacteriophages that are specific for particular bacteria.

Also, U.S. Pat. No. 4,957,686 (Norris) discloses a procedure of improved dental hygiene which comprises introducing into the mouth bacteriophages parasitic to bacteria which possess the property of readily adhering to the salivary pellicle.

Despite the recognized value and importance of new antimicrobial therapies, the potential of phage therapy has not been accomplished in any practical sense that is used in modem therapeutics, nor have methods, compositions, or other uses been defined for nontoxic and efficacious therapies of this type with practical and effective delivery. In particular for efficient prevention and treatment of infections related to *E. coli*, such as diarrhea diseases.

In fact, *E. coli* is an extremely well-investigated bacterium, with two completely sequenced members, the non-pathogenic strain K-12 (Blattner, F. R., et al., 1997 Science 277, 1453-1474) and the pathogenic strain 0157:H7 (Perna, N. T. et al., 2001, Nature 409, 529-533; Hayaslis et al., 2001, DNA Research 8, 11-22) which resembles enteropathogenic *E. coli* (EPEC) strains.

Although, two *E. coli* phages (lambda and T4) are the most carefully characterized biological systems (Karam, J. D., 1994, Molecular biology of bacteriophage T4. ASM Press, Washington, D.C.), there still exists a need to develop new and useful phage therapeutics which can be used to prevent or to treat infectious disorders caused by such bacterial microorganisms, such as *E. coli* serotypes associated with diarrhea of children and the traveler.

There also exists a need to develop compositions including phage therapeutics in acceptable vehicles that can be administered to subjects infected with bacterial microorganisms.

Finally, there exists a need to develop a bacteriophage preparation that is virulent and non-toxic thereby rendering it useful in treating bacterial infections related to pathogenic *E. coli* or *Salmonella*.

SUMMARY OF THE INVENTION

It is therefore an object of the present invention to develop new and useful phage therapeutics which can be used to prevent or to treat infectious disorders caused by pathogenic Enterobacteriaceae such as *E. coli* infections, in particular diarrheal or urinary diseases in humans or animals, or *Salmonella* infections.

Another object of the invention is to provide isolated bacteriophage preparations with substantial lytic potential towards pathogenic Enterobacteriaceae such as *E. coli* and/or *Salmonella* strains that is virulent and non-toxic.

It is also an object of the present invention to provide the use of such bacteriophage preparations in various nutritional compositions, pet food products, supplements or pharmaceutical compositions for the treatment or prevention of infections caused by pathogenic *E. coli* and/or *Salmonella* in humans or animals.

It is a further object to provide a nutritional composition, a pet food product, a supplement, or a pharmaceutical composition comprising at least one phage as described above.

It is yet another object of the present invention to provide a method of prevention or treatment of infections caused by pathogenic Enterobacteriaceae such as *E. coli* and/or *Salmonella* in humans or animals using phage therapeutics in nutritional compositions, pet food, supplements or pharmaceutical preparations.

A major advantage of the present invention is that the bacteriophage preparations selected according to the invention have a broad host range on causing-causing *E. coli* strains, they are non toxic, so that they may be used safely in food compositions for an efficient prevention or treatment of infections caused by pathogenic *E. coli*. The phages according to the invention can also be used for industrial applications. They can efficiently be propagated on a non-pathogenic *E. coli* strain while retaining a broad host range. The phages kill efficiently the host cell and the phages can be highly purified by a standard virus isolation method.

DETAILED DESCRIPTION OF THE INVENTION

Within the following description, "NCC" designates Nestle Culture Collection (Nestle Research Center (NRC), Vers-chez-les-Blanc, Lausanne, Switzerland).

According to a first aspect, a broad-host range Myoviridae phage isolates with substantial lytic potential towards pathogenic Enterobacteriaceae such as *E. coli* and/or *Salmonella* strains have been isolated from human stool samples and the environment.

Stool samples from children hospitalized with acute diarrhea were screened with the plaque assay for the presence of bacteriophages directed against *E. coli*. Different source of water has also been screened for the presence of bacteriophages. These waters (tap, sewage, drain, pond, canal, street and market water) are from Dhaka/Bangladesh and from Lausanne (sewage water). About 45 myoviridae phages were isolated and amplified on the non-pathogenic laboratory *E. coli* K-12. These isolates showed a broad host range on a large collection of pathogenic *E. coli* strains. Phages could be purified by standard methods of virus purification. All phages investigated in detail turned out to be T4-like phages (obligate virulent phages with contractile tail). The diagnosis was based on the large genome size (170 kb), modification of the DNA (resistance against digestion with restriction endonucleases) and morphology.

They can efficiently be propagated on a non-pathogenic *E. coli* strain while retaining a broad host range on diarrhea-causing *E. coli* strains. The T4-like phages kill efficiently the host cell. They are the prototype virulent phages that destroy the bacterial genome during the infection process. This property adds substantially to the safety of the phage therapy approach.

In a preferred embodiment, the phages are selected from the group comprising NCCJS9, NCC-JS31, NCC-JS102.2, NCC-JS150, NCC-JS1, NCC-JS10 (renamed NCC-JS4) (CNCM I-2763), NCC-JS22, NCC-JS32, NCC-JS114.1, NCC-JS140.1, NCC-JS146.1, NCC-JS65.1, NCC-JS65.2', NCC-JS76.2', NCC-JS12, NCC-JS152, NCC-JS66, NCC-JS102.1, NCC-JS140.2, NCC-JS146.2, NCC-JS61.2, NCC-JS61.3, NCC-JS114.3, NCC-JS35 (renamed NCC-JS94.1) (CNCM I-2764), NCC-JS94.2, NCC-JS98, NCC-JS104, NCC-JS94.3, NCC-JS110.1, NCC-JS110.2, NCC-JS110.3, NCC-JS1.4 (renamed NCC-JSD.1) (CNCM I-2765), NCC-JSD.3, NCC-JSD.2, NCC-JSD.4, NCC-JSD.5, NCC-JS142, NCC-JS148 and NCC-JSL.1, NCC-JSL.2, NCC-JSL.3, NCC-JSL.4, NCC-JSL.5, NCC-JSF (renamed NCC-JSL.6) (CNCM I-2766).

In a most preferred embodiment, the phages NCC-JS10, NCC-JS35, NCC-JS1.4 and NCC-JSF have been deposited by way of example at the Institut Pasteur, 28 rue du Docteur Roux, F-75024 Paris cédex 15, FRANCE, on Dec. 11, 2001, under the deposit number CNCM I-2763, CNCM I-2764, CNCM I-2765 and CNCM I-2766.

Advantageously, the phages deposited, for example, are able to lyse 42 per cent of the diarrhea-causing *E. coli* Nestlé Research Center collection composed of 50 strains. This collection represents the major *E. coli* serotypes of childhood diarrhea in developing countries and traveler's diarrhea. With the phage material according to the invention, coverage of 60 percent can be obtained with an increase of individual phage isolates included into the cocktail.

There is, however, no risk to other commensal gut bacteria outside of the species *E. coli*. The ecological equilibrium of the gut is maintained (see example 3, FIG. 2). After a phage treatment of mice, no phages are any longer present in the intestine.

With the phage material according to the invention, only less than 50 percent of nonpathogenic human gut *E. coli* serotypes are attached.

Thus, according to a further aspect, the invention relates to the use of at least one phage isolate as described above, in any food or pharmaceutical product, or a nutritional supplement or a composition for oral administration. Examples for food or pharmaceuticals products are milk, yogurt, curd, cheese, fermented milks, milk based fermented products, ice-creams, fermented cereal based products, milk based powders, infant formulae or tablets, liquid suspensions, dried oral supplement, wet oral supplement, dry-rube-feeding, pet food products. The composition for oral administration may be in capsules, soft capsules, tablets, pastes or pastilles, gums, or drinkable solutions or emulsions. Methods for preparing them are common knowledge.

The composition according to the invention may also comprise usual excipients, in particular sweeteners, flavoring agents or preservatives. It can further comprise a prebiotic and/or a probiotic micro-organism. The compositions of the invention may be formulated according to anyone of a number of techniques that are well known to this art.

In one embodiment, a pharmaceutical composition containing at least one of the bacteriophages in an amount sufficient to achieve the desired effect in an individual can be prepared. This composition may be a tablet, a liquid, a dried oral supplement, a wet oral supplement, dry tube-feeding, wet tube-feeding etc. The pharmaceutical composition will further contain carriers and excipients that are suitable for delivering the respective active molecule of different nature to the target tissue. The kind of the carrier/excipient and the amount thereof will depend on the nature of the substance and the mode of drug delivery and/or administration contemplated. It will be appreciated that the skilled person will, based on his own knowledge, select the appropriate components and galenic form.

In another embodiment, a food composition for human consumption is prepared. This composition may be a nutritional complete formula, a dairy product, a chilled or shelf stable beverage, water, a soup, a dietary supplement, a meal replacement, a nutritional bar or a confectionery.

The nutritional formula is preferably enterally administrable; for example in the form of a powder, a liquid concentrate, or a ready-to-drink beverage. If it is desired to produce a powdered nutritional formula, the homogenized mixture is transferred to a suitable drying apparatus such as a spray drier or freeze drier and converted to powder.

In a preferred embodiment, phages may be added to a milk formula with lukewarm water and could be of benefit to children suffering from *E. coli* gastroenteritis or *Salmonella* infections, or are at risk to acquire such infections. Pediatric *E. coli* diarrhea is rare in industrial countries of the Northern hemisphere, however, these infections are still very prevalent in countries like Mexico, Brazil, India and China.

Also, phages may be used in the prevention or treatment of traveler's diarrhea. European tourists spending their holidays in Northern Africa or US American tourists traveling to Central America or the Caribbean are at high risk to acquire ETEC infections.

Also, *E. coli* infections are a frequent cause of urinary infections in humans, including industrial countries. The O serotypes of extra-intestinal *E. coli* isolates differ from those of intestinal *E. coli* strains. However, the broad host-range of many T4-like phages leave no doubt that many of the urinary *E. coli* strains can be lysed with T4 phages isolated from stool samples.

In another embodiment, a usual food product may be enriched with at least one phage isolate according to the present invention. For example, a fermented milk, a yogurt, a fresh cheese, a renneted milk, article of confectionery, for example a sweet or sweetened beverage, a confectionery bar, breakfast cereal flakes or bars, drinks, milk powders, soy-based products, non-milk fermented products or nutritional supplements for clinical nutrition.

The bacteriophages according to the present invention may thus be used in an amount of at least $1.10^4$ pfu (plaque forming unit)/ml and more preferably $10^6$ pfu/ml.

In a further embodiment, pet food products may be prepared. In fact, *E. coli* is the major cause of diarrhea in dogs. The serotypes of EPEC and ETEC strains isolated from dogs partially overlap those of humans. Dogs harbor in their intestine *E. coli* serotypes that frequently lead to smear infections in the urinary tract. This canine urinary tract *E. coli* isolates showed close genetic relationships with human extra-intestinal *E. coli* isolates. The pet food formulation is preferably a complete and nutritionally balanced pet food. It can also be a dietary supplement for pets or in the form of a pharmaceutical composition. The nutritionally complete pet food formulation according to the invention may be in any suitable form, for example a powder, a dried kibble, or pellet or other dried form, extruded form, semi-moist or wet form, such as a chunk or loaf or pudding. It may be chilled or provided as a shelf stable product. This pet, food may be produced by conventional methods.

In another embodiment, dietary adjuncts may be prepared so as to improve pet food quality. As dietary adjuncts, they may be encapsulated or may be provided in powder form and packaged in conjunction with or separately from a main meal, be it wet or dry. By way of example, a powder containing bacteriophages according to the invention may be packed in sachets in a powder form or in a gel or lipid or other suitable carrier. These separately packaged units may be provided together with a main meal or in multi-unit packs for use with a main meal or treat, according to user instructions.

Also, oral application of phages according to the invention or spraying of phages in the household could thus benefit both the dog and the pet owner.

In a last embodiment, phages may be of value in food production to decrease the degree of contamination of meat with *E. coli* and/or *Salmonella*.

The following examples are given by way of illustration only and in no way should be construed as limiting the subject matter of the present application. All percentages are given by weight unless otherwise indicated. The examples are preceded by a brief description of the figures.

FIG. 1: growth curve (OD readings) of *E. coli* K12 in presence of T4-like phage NCC-J146.1 and NCC-JS94.1. Cultures of *E. coli* K12 were grown to an OD of 0.1 and infected with 1% of the above phages. Samples were taken each 10 minutes.

Figure 2:
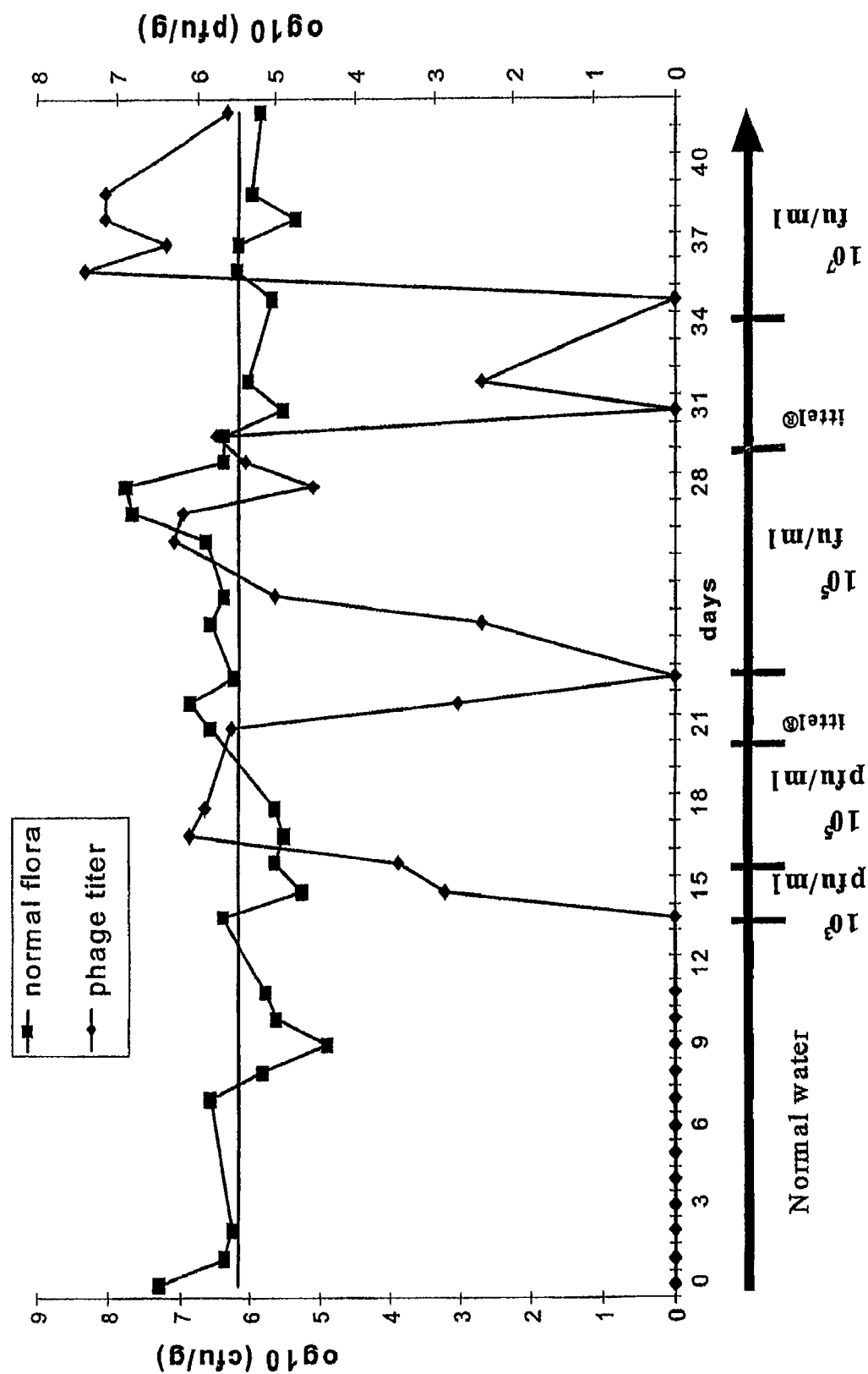

FIG. 2: in vivo studies in mice. *E. coli* flora of four mice was monitored for 42 days. A mix of bacteriophage (NCC-JS94.1, NCC-JS4, NCC-JSD.1 and NCC-JSL.6) has been added to the water three times at different concentration (with three changes of water). A control mouse has received the same water (with the same changes) without the phage mix. Feces have been recovered once or twice a day. Bacteriophage mix has been isolated titrated and *E. coli* flora was determined. The linear bar represents the average of the normal flora.

Figure 3:
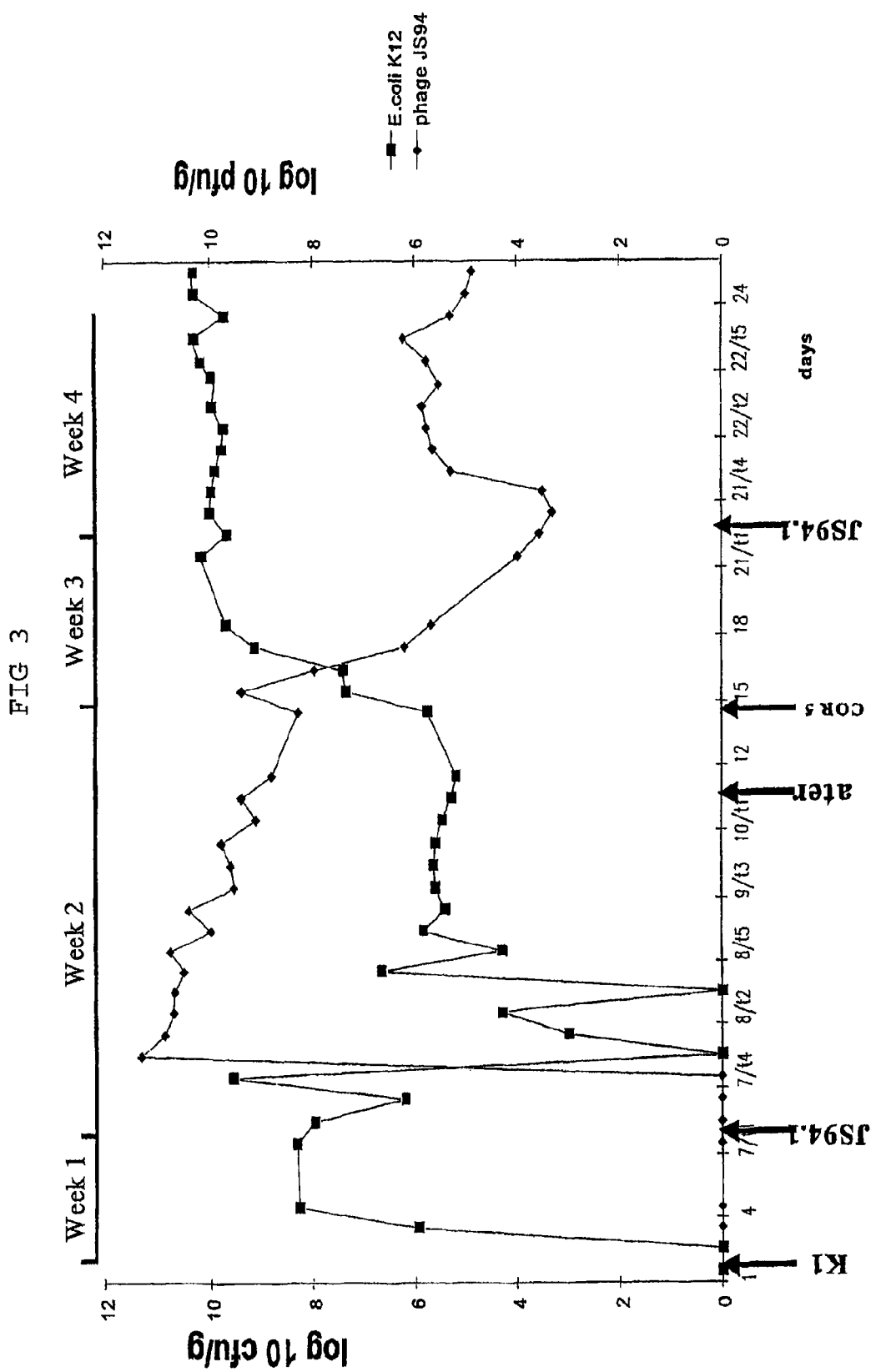

FIG. 3: Phage infection on axenic mice. Two axenic mice were: force fed with *E. coli* K-12 and phage NCC-JS94.1 was added to the water at a final concentration of $10^5$ pfu/ml for a week. Normal flora and presence of phages on the feces was monitored all along the trial. In the third week, mice were again force fed with ECOR5 which is resistant to the phage. NCC-JS94.1 was again added to the water and feces were recovered and tested for the presence of *E. coli* and the phage.

Figure 4A:
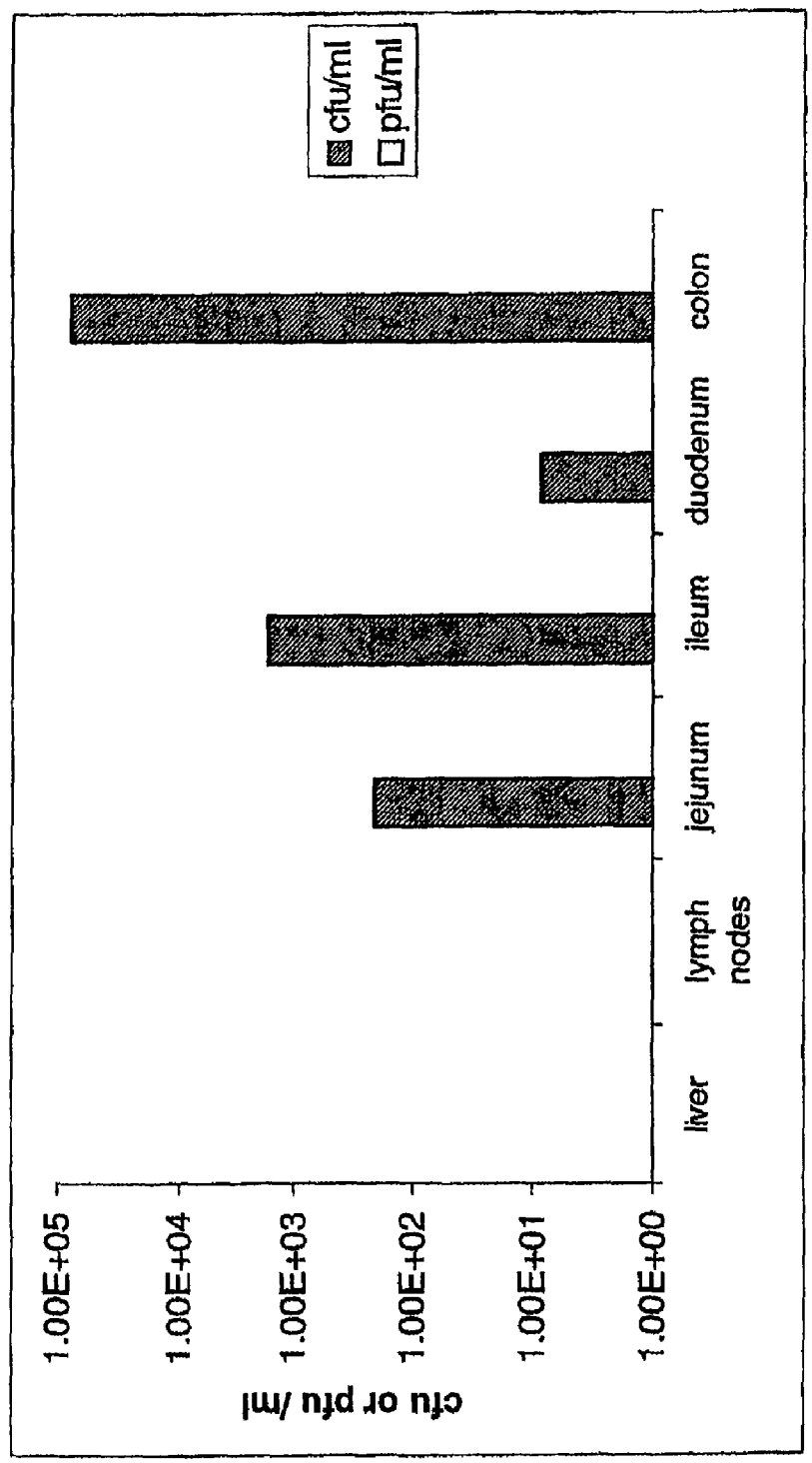
Figure 4B:
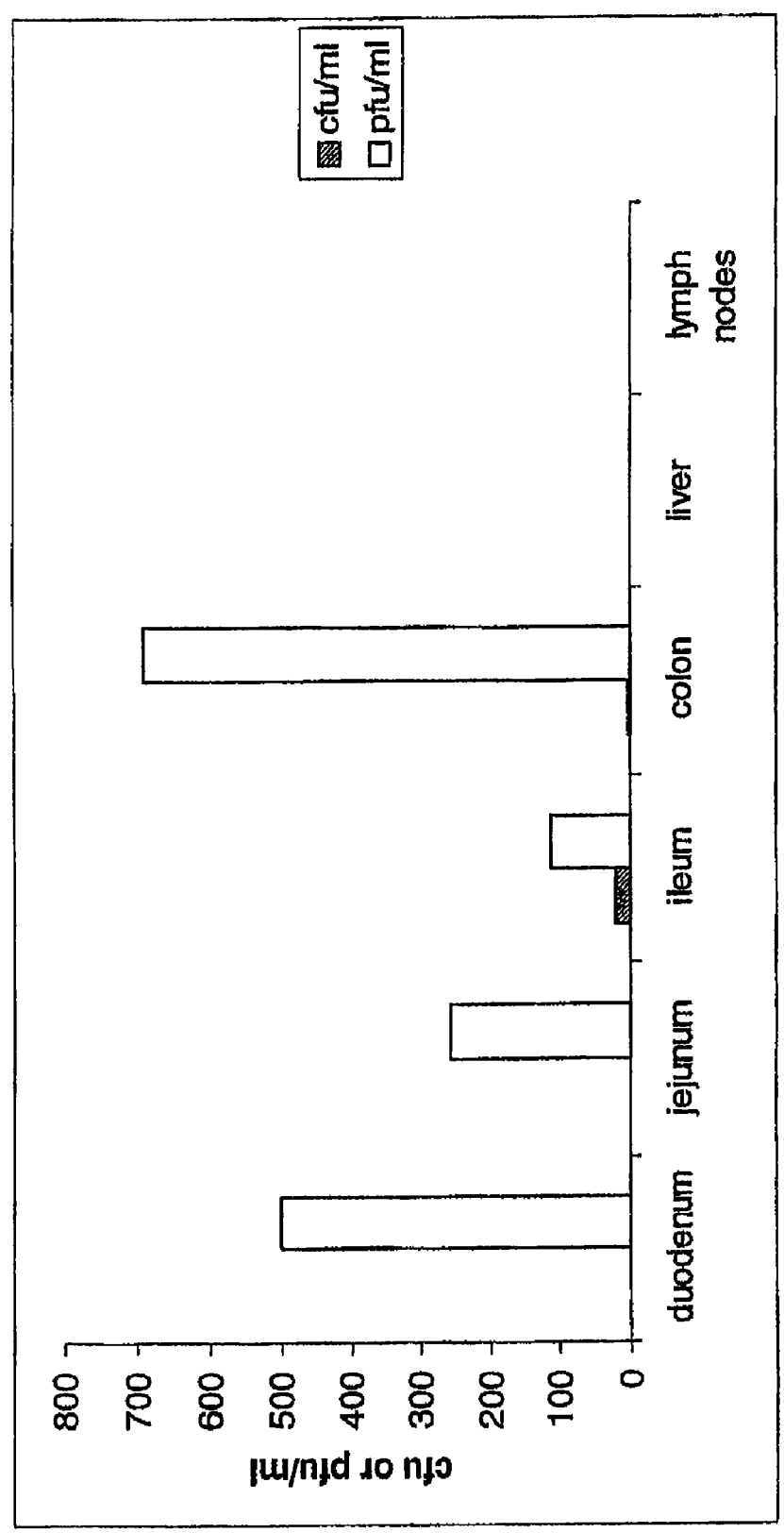

FIG. 4: Autopsy were performed after a phage treatment of four mice, when no more phages where recovered from the feces (FIG. 4A) and while four other mice were treated with phages (FIG. 4B). Different part of the intestine (duodenum, jejunum, ileum, colon), the liver and lymph nodes were collected and tested for the presence of *E. coli* and phages. Column represents the average for each group of mice.

EXAMPLES

Example 1

Selection of Phages According to the Invention

Material and Methods
Preparation of Stools Samples

The stool samples were stored frozen at ~20° C. at the hospital and were transported on dry ice to Lausanne. The thawed stool sample (~10 g) was resuspended in TS (8.5 g/l NaCl, 1 g/l tryptone) to a final volume of 30 ml. The resuspended stool samples were then centrifuged for 15 minutes at 10.000 rpm in 50 ml Falcon tubes. One ml of each stool was filtered through a Millex AP20 prefilter followed by a 0.45 µm Minisart filter. After resuspension all stool samples were stored at +4° C. since T4 phages are sensitive to repeated cycles of freezing/thawing.

Bacterial Culture

All *E. coli* strains were propagated on Hershey broth containing 2 ml of thiamine (2 mg/ml) per liter in a glass-tube in a final volume of 5 ml under agitation (240 rpm) at 37° C. for overnight incubation. After growth, the strains were streaked on a Petri dish (Hershey agar) in order to obtain single colonies. To avoid serial passages in broth (which could select for mutants), a new culture was initiated from 3 single colonies each time when needed. The stock cultures were kept as stab-cultures at 4° C.

Plaque Assay

Phage plaques were obtained on Hershey agar supplemented with thiamine overlayed by 3.5 ml of Hershey top-agar inoculated with 200 µl of a fresh grown overnight culture and 100 µl of stool sample or cell lysate. The Petri dishes were incubated overnight at 37° C.

Isolation of Plaques and Phage Amplification

Single plaques were picked with toothpicks and inoculated in 5 ml of Hershey broth supplemented with thiamine were inoculated with 1% of a freshly grown culture and 1% of phage lysate. Incubation was performed under agitation at 240 rpm at 37° C. for approximately 5 hours. When the lysis occurred, 3 drops of chloroform was added by gentle mix. The lysate was left overnight at room temperature followed by a centrifugation at 10,000 rpm for 10 minutes. To obtain phage stocks the supernatant was recovered by carefully avoiding the chloroform and transferred into a screw-cap glass tube. Three drops of fresh chloroform were added and the phage stock was stored at 4° C. The strains used for phage amplification were either K-12 or 0127:K63 (B74-9). The following nomenclature was used for the different phage isolates: JS (the initials of Josette Sidoti who conducted the phage survey) followed by the patient ID number. In case of multiple isolates from the same patient, this number was followed by a further number (e.g. JS61.2). When the second isolate came from a second (convalescent) stool sample of the patient, the second number was primed (e.g. JS65.2'). For phages isolated from environmental water the initials were followed by a D (Dhaka) or L (Lausanne), respectively, and an identifier for the phage isolate (e.g. JSL4).

Spot-Test

A mixture of 3.5 ml Hershey top-agar with 200 µl of a freshly grown E. coli culture was poured on a bottom layer of Hershey agar supplemented with thiamine. When the top-agar was solidified, 10 µl of filtered extracted stool was put on it as 8 spots in clockwise distribution. Incubation was done overnight at 37° C.

Lysis in Tubes 5 ml of Hershey broth inoculated with 1% of a freshly grown culture. Incubation was continued for 3 to 5 hours when the uninfected control cells reached the stationary growth phase. The optical density in the phage-inoculated cell was compared visually with the optical density in the mock-infected control cell.

Phage Purification

For purification of the T4-like phages, one liter of Hershey medium containing thiamine was inoculated 1% with K-12, cells were grown to an OD of 0.1 and then infected with a moi (multiplicity of infection) in excess of 1. NaCl was added to the lysate yielding a final concentration of 0.5M and incubated one hour at 4° C. After centrifugation at 10,000 rpm (16 min at 4° C.) in a Sorvall RC5B centrifuge, polyethylenglycol PEG-6000 was added to the supernatant to a final concentration of 10%. The lysate was incubated overnight at 4° C. under gentle stirring. PEG-precipitated phages were collected by centrifugation at 10,000 rpm for 16 min, the resulting pellets were resuspended in 3 ml of phage buffer (20 mM Tris-HCl pH 7.4, 100 mM NaCl, 10 mM $MgSO_4$). The resuspended phage pellet was applied onto a discontinuous CsCl gradient (1.35 g/ml CsCl, 1.53 g/ml, 1.65 g/ml). The gradients were centrifuged in a SW55 rotor at 40,000 rpm for 3 h at 4° C. with Beckman L860M ultracentrifuge.

Results

Isolation of Phages

E. coli phages can be isolated from clinical material (e.g. stool) or environmental samples (e.g. sewage). Previous work suggested that phages are only rarely isolated from stool samples of healthy subjects, phage titers were low and most isolates were temperate phages (Furuse, K., 1987, Distribution of coliphages in the environment: general considerations. In: Phage Ecology, pp. 87-124, J. Wiley, New York). Stool samples from diarrhea patients, in contrast, yielded phages with higher incidence and higher titer than stool samples from healthy controls and most isolates were virulent phages. To increase the likelihood for T4-like phage isolation we worked with stool samples from children hospitalized with acute diarrhea in the general ward of a large diarrhea clinic in Dhaka/Bangladesh. The statistical aspects of the phage screening are summarized in Table 1.

TABLE 1

Phage screening statistics

| | |
|---|---|
| No. of consecutive patients with acute diarrhea enrolled in the screening program | 157 |

TABLE 1-continued

Phage screening statistics

| | |
|---|---|
| No. of patients with paired acute and convalescent stool samples subset of above) | 52 |
| No. of stool samples excluded from anal sis | 17 |
| Reason for exclusion | Confirmed Cholera or Shigella infections |
| Sampling period | 6.2.2000 to 25.2.2000 |
| Place | Dhaka/Bangladesh |
| Patient age (range) | 1 month to 4 years |
| Sex (M:F) | 96:61 |
| No. of patients yielding phage plaques on K12 indicator cell/no. tested (% positive) | 26/140(19) |
| Range of phage titers (pfu/g stool) | 30* –5 × $10^4$ |
| No. of patients with titer >$10^3$/>$10^4$ pfu/g | 10/6 |
| No. of stool samples yielding phage plaques on B74-9 for presence of phage | 118 |
| negative on both | 86 |
| positive on both | 4 |
| positive only on K12 | 14 |
| positive only on B74-9 | 14 |

Notes:
*Detection limit of the test
Average etiology of diarrhea diseases in Bangladeshi children <3 years: rotavirus 26%, Campylobacter 26%, E. coli 15%, V. cholerae 01 7%, other Vibrios 9%, Shigella 4%, Salmonella <1%.

Stool samples from 157 acute diarrhea patients were taken over a three-week time period. The patients were unselected and the sampling was done according the availability of the nurses to take and store a stool sample. For 52 patients a second stool sample was obtained at the discharge from the hospital. Seventeen stool samples were excluded since an E. coli diarrhea could be excluded: 5 patients had cholera (as demonstrated by dark-field microscopy of vibrios in rice stools) and 12 had Shigella dysentery (diagnosed on clinical grounds: bloody, mucous stools). Together both pathogens account to 11 percent of the hospitalized patients. This figure corresponds to the average detection rate of these pathogens in diarrhea patients from this hospital (Vibrio cholerae 7%, Shigella spp. 4%).

With a detection limit of 30 pfu (plaque forming units)/g feces, 19 percent of the stool samples scored positive when tested on the non-pathogenic laboratory E. coli strain K-12. The highest amount of phage shed into the stool by any of the patients was 5×$10^4$ pfu/g feces. However, only 4 percent of the patients showed such high stool phage titers. A somewhat lower percentage of patients showed phages that could be detected on the pathogenic EPEC strain 0127:K63 (14% detection rate). Only four stool samples were doubly positive for phages on the laboratory and pathogenic E. coli strain, while 14 were positive only for K-12 and 14 other only for EPEC strain O127:K63. Apparently we detected with the two different E. coli indicator cells two distinct phage populations with minimal overlap in host range. Interestingly, the phage detection rate of 14% on the pathogenic E. coli indicator cell corresponded closely to the average detection rate of pathogenic E. coli strains in the stool samples from diarrhea patients in Bangladesh (15%).

Different sources of water (tap, drain, refuse, canal, pond, sewage, market, street, river, ditch waters) from Dhaka/Bangladesh has also been screened for the presence of phages. From almost a hundred samples (about 10 of each source of water), six different bacteriophages have been obtained and amplified. One of them was from tap water, three from drain water and one from sewage water. Sewage waters from Lausanne (Switzerland) have also yielded to six phage isolates.

On the laboratory E. coli strain, the detection rate of phages was lower in the convalescent than in the acute stool sample (4 vs. 11 positive samples, 52 paired stool samples studied).

On the pathogenic *E. coli* strain comparable numbers of phages were isolated from convalescent and acute stool samples (5 vs. 4 positive samples, 16 stool samples studied).

All plaques detected on K-12 cells could be amplified in liquid culture growth on K12. Phage titers ranged from $2\times10^4$ to $4\times10^{10}$ pfu/ml. The median titer was $10^9$ pfu/ml. There was no correlation between the amplified titer and plaque size (large, medium, small or pinpoint), plaque transparency (turbid, clear) or initial stool titer. Similarly, plaques detected on the EPEC strain O127:K63 could be amplified to $1-5\times10^8$ pfu/ml on this pathogenic *E. coli* strain.

Target Population of Causing—Causing *E. coli* Strains

The phage isolates were selected with the broadest host range on 50 pathogenic *E. coli* strains from the major serotypes isolated worldwide from pediatric diarrhea patients. Table 2 shows some of these strains. This set of strains covers 14 different somatic O antigens reflecting distinct carbohydrate side chains of the lipopolysaccharide antigen (LPS) and also 14 different capsular antigens K reflecting again different polysaccharide compositions of the bacterial capsular material. In addition, we possess a collection of the major enterotoxigenic *E. coli* (ETEC) serotypes isolated worldwide from both pediatric gastro-enteritis patients and adult traveler's diarrhea (Table 2). These ETEC strains represent 14 further distinct O antigens and 13 different H antigens. The latter antigen is a protein antigen from the bacterial flagellum. The ETEC strains could be further subdivided according to their production of enterotoxins. Eight strains produced heat labile (LT) and heat stabile (ST) enterotoxins. Two strains produced only the heat labile; four strains only the heat stabile enterotoxin.

TABLE 2

Pathogenic type, O-, K- and H-serotype of the causing-causing *E. coli* strains from the Nestec collection

| Nestec code | O:K (H) serotype | Pathogenicity type: Virulence factors | stool phages |
|---|---|---|---|
| B74-20 | O18:K77 | EPEC | 16 |
| B74-24 | O20:K84 | EPEC | 4 |
| B74-7 | O26:K60 | EPEC | 10 |
| B74-26 | O44:K74 | EPEC | — |
| B75-45 | O55:K59 | EPEC | 7 |
| B74-10 | O86:K61 | EPEC | 13 |
| B74-1 | O111:K58 | EPEC | 10 |

TABLE 2-continued

Pathogenic type, O-, K- and H-serotype of the causing-causing *E. coli* strains from the Nestec collection

| Nestec code | O:K (H) serotype | Pathogenicity type: Virulence factors | stool phages |
|---|---|---|---|
| B74-28 | O112:K66 | EPEC | 6 |
| L74-30 | O119:K69 | EPEC | 5 |
| B75-46 | O124:K72 | EPEC | 0 |
| B74-14 | O125:K70 | EPEC | 5 |
| B74-16 | O126:K71 | EPEC | — |
| B74-9 | O127:K63 | EPEC | — |
| M75-53 | O128:K67 | EPEC | — |
| R81-116 | O6:H16 | ETEC: LT+/ST+ | 15 |
| R81-117 | O8:H9 | ETEC: LT+/ST+ | 0 |
| R81-118 | O15:H11 | ETEC: LT+/ST+ | 12 |
| R81-119 | O25:H42 | ETEC: LT+/ST+ | 12 |
| R81-120 | O78:H12 | ETEC: LT+/ST+ | 11 |
| R81-121 | O115:H51 | ETEC: LT+/ST+ | 8 |
| R85-141 | O128:H18 | ETEC: LT+/ST+ | 0 |
| R85-145 | O148:H28 | ETEC: LT+/ST+ | 14 |
| R85-147 | O114:H49 | ETEC: LT+/ST− | — |
| R85-149 | O159:H21 | ETEC: LT+/ST− | — |
| R85-137 | O20:H11 | ETEC: LT−/ST+ | 7 |
| R85-138 | O27:H7 | ETEC: LT−/ST+ | 1 |
| R85-144 | O63:H- | ETEC: LT−/ST+ | — |
| R85-152 | O153:H12 | ETEC: LT−/ST+ | 9 |

Note:
The first column gives the internal NRC code for the *E. coli* strain; the second column provides the somatic O, capsular K or flagellar H serotype of the strain, the bold O serotypes indicate *E. coli* strains also isolated from canine diarrhea (Sancak, 1997); the third column indicates the pathogenic type (EPEC: enteropathogenic; ETEC: enterotoxigenic *E. coli*; LT, ST are heat-labile and heat-stabile enterotoxin); the fourth column indicates the number of the stool phage isolates that lysed the indicated *E. coli* strain (32 stool phage isolates were tested).

Host Range Screening of the Isolated Phages

In the first round 32 phages were isolated from the stool samples of the diarrhea patients. These phages were systematically tested on the 50 causing-causing *E. coli* strains from our combined cell collection. In a second round further phage isolates with broad host range were obtained.

As the host range testing involves a large number of phage-cell combinations (n=32×50=1600 on 50 *E. coli* strains), we used the spot test for screening. In this test, eight different amplified phage lysates can be tested at the same time by spotting a drop of the amplified phage lysate on the bacterial lawn in a Petri dish. The results are read after overnight incubation and are scored as positive when the growth of the bacteria was compromised or impeded over the spotted area. The results of some phage isolates are presented in Table 3 and are summarized in Table 4.

TABLE 3

Susceptibility of the indicated *E. coli* strains to infection with stool phage isolates JS1 to JS16 propagated on K-12 (K) or O127:K63 (B) as assessed by the spot assay

| | Phage JS | | | | | | | | | | | | |
|---|---|---|---|---|---|---|---|---|---|---|---|---|---|
| | 146.1 | 146.2 | 65.1 | 65.2 | 61.1 | 77.1 | 83.1 | 114.2 | 114.1 | 4 | 66 | 76.2 | 12 |
| *E. coli* | K | K | K | K | B | B | B | B | K | K | K | K | K |
| ETEC LT+/ST+ | X | X | X | X | | | | | X | X | X | X | X |
| ETEC LT+/ST+ | | | | | | | | | | | | | |
| ETEC LT+/ST− | X | X | X | X | | | | | X | X | X | X | X |
| ETEC LT+/ST− | | | | | | | | | | | | | |
| ETEC LT+/ST− | X | X | X | X | | | | | X | X | X | X | X |
| ETEC LT+/ST+ | X | X | X | X | | | | | X | X | X | X | X |
| ETEC LT+/ST+ | | | | | | | | | | | | | |
| ETEC LT+/ST− | X | X | | | | | | | | X | X | X | X |
| ETEC LT+/ST− | | | | | | | | | | | | | |
| ETEC LT+/ST− | X | X | X | X | | | | | X | X | X | X | X |
| EPEC: A/E+ | X | X | X | X | | | | | X | X | X | X | X |
| EPEC: A/E+ | X | X | | | | | | | | X | X | X | |
| EPEC: A/E+ | X | X | X | X | | | | | | X | X | X | X |

TABLE 3-continued

Susceptibility of the indicated *E. coli* strains to infection with stool phage isolates
JS1 to JS16 propagated on K-12 (K) or O127:K63 (B) as assessed by the spot assay

| | Phage JS | | | | | | | | | | | | |
|---|---|---|---|---|---|---|---|---|---|---|---|---|---|
| | 146.1 | 146.2 | 65.1 | 65.2 | 61.1 | 77.1 | 83.1 | 114.2 | 114.1 | 4 | 66 | 76.2 | 12 |
| EPEC: A/E+ | | | | | | | | | | | | | |
| EPEC: A/E+ | X | X | X | X | | | | | X | X | X | X | X |
| EPEC LT+/ST+; CFA 1 | X | X | | | | | | | | X | X | | |
| ETEC LT−/ST+; CS4; CS6 | X | X | X | X | | | | | | X | X | X | X |
| ETEC LT−/ST+; CS6 | | | | | | | | | | | | X | X |
| ETEC LT−/ST+; PCF O166 | X | X | X | X | | | | | X | X | X | X | X |
| ETEC LT+/ST+; CS1; CS3 | X | X | X | X | | | | | X | X | X | X | X |
| ETEC LT−/ST+; CFA1 | X | X | X | X | X | X | | | X | X | | X | X |
| ETEC LT−/ST+; CS4; CS6 | X | X | | | | | | | | X | X | X | X |
| ETEC LT+/ST+; CS1; CS3 | X | X | X | X | | | | X | X | X | X | X | X |
| ETEC LT+/ST+; CS5; CS6 | | | | | | | | | | | | | |
| ETEC LT+/ST+; CS5; CS6 | | | | | | | | | | | | | |
| EPEC | X | X | X | X | X | | | | X | X | | X | X |
| EPEC | X | X | X | X | X | | | | X | X | X | X | X |
| EPEC | X | X | X | X | | | | | X | X | X | X | X |
| ETEC O6:H16 | X | X | X | X | | | | | X | X | X | X | X |
| ETEC O8:H9 | | | | | | | | | | | | | |
| ETEC O15:H11 | X | X | X | X | | | | | X | X | X | X | X |
| ETEC O25:H42 | X | X | X | X | | | | | X | X | X | | X |
| ETEC O78:H12 | X | X | | | | | | | | X | X | X | X |
| ETEC O115:H51 | X | X | | | | | | | | X | X | X | X |
| ETEC O20:H11 | X | X | X | X | | | | | | X | X | | |
| ETEC O27:H7 | | | | | | | | | | X | | | |
| ETEC O128:H18 | | | | | | | | | | | | | |
| ETEC O63:H− | X | X | | | | | | | X | X | X | | |
| ETEC O148:H28 | X | X | X | X | | | | | X | X | X | X | X |
| ETEC O153:H12 | | | | | | | | | | | | X | X |
| EPEC O18:K77 | X | X | X | X | | | | | X | X | X | X | X |
| EPEC O20:K84 | X | X | | | | | | | | X | X | | |
| EPEC O26:K60 | X | X | | | | | | | | X | X | X | X |
| EPEC O55:K59 | | | X | | | | | | X | | | | X |
| EPEC O86:K61 | X | X | X | X | X | | | | X | | | X | |
| EPEC O111:K58 | X | X | X | X | | | | | | X | X | | X |
| EPEC O112:K66 | | X | X | X | | | | X | | X | | | |
| EPEC O119:K69 | X | X | | | | | | | | X | X | | |
| EPEC O124:K72 | | | | | | | | | | | | | |
| EPEC O125:K70 | X | X | | | | | | | | X | X | | |

Notes for Table 3:
Susceptibility of the *E. coli* strain indicated in the first column to infection with the phage strain indicated in the first row. See Table 5 for further characterization of the phage strains.
The second row provides information on the *E. coli* strain on which the phage was propagated (K.: non-pathogenic K-12; O: pathogenic O:127:K63).
"X" indicates growth inhibition in the spot test,
blank means growth as control spot (mock infection).

When distinct phage isolates from the same patient were compared, nearly identical results were obtained. For example, two different plaques were amplified from the stool sample of patient 146. Phage NCC-JS146.1 scored positive on 35 cells, while phage NCC-JS146.2 infected 36 out of the 50 tested phages. With one exception, there was a perfect overlap between both phages with respect to the host range (Table 3). Similar overlaps were seen for two phages isolated from the acute and the convalescent stool sample of a single patient: phages NCC-JS65.1 and NCC-JS65.2' of patient 65 infected 26 and 25 *E. coli* strains, respectively. Again with one exception, there was a perfect overlap in host range (Table 3). This high correlation of results between independent phage isolates from the same patient proves the reliability of the spot test.

The host range was drastically different for phages propagated on the non-pathogenic laboratory strain K-12 or the pathogenic strain O127:K63. The former phages could grow on a median of 26 different pathogenic *E. coli* strains, while the latter grew only on a median of 1 pathogenic strain in addition to the propagating cell (Table 4). This is illustrated for the stool sample of patient 114 which was one of the few stool samples (n=3) that yielded phages on both K-12 and O127:K63. The K-12-amplified phage infected 24 pathogenic strains, while the O127:K63-amplified phage infected only a single strain (Table 4).

TABLE 4

Characterization of the 36 phages isolated from the stool samples of the pediatric diarrhea patients in Dhaka

| Code | Propagating strain | Plaque size | Spot test positive |
|---|---|---|---|
| NCC-JS9 | K | m | 33 |
| NCC-JS31 | K | g | 27 |
| NCC-JS102.2 | K | m | 9 |
| NCC-JS150 | K | s | 3 |
| NCC-JS61.1 | B | s | 5 |
| NCC-JS77.1 | B | pp, t | 0 |
| NCC-JS83.1 | B | s, t | 1 |
| NCC-JS20 | B | s | 7 |
| NCC-JS1 | K | m | 28 |
| NCC-JS4 | K | m | 35 |

TABLE 4-continued

Characterization of the 36 phages isolated from the stool samples of the pediatric diarrhea patients in Dhaka

| Code | Propagating strain | Plaque size | Spot test positive |
|---|---|---|---|
| NCC-JS22 | K | m | 17 |
| NCC-JS32 | K | s | 21 |
| NCC-JS114.1 | K | m, t | 24 |
| NCC-JS | K | m | 6 |
| NCC-JSI46.1 | K | s | 35 |
| NCC-JS65.1 | K | s | 26 |
| NCC-JS65.2' | K | m | 25 |
| NCC-JS89 | B | m | 1 |
| NCC-JS114.2 | B | s, t | 1 |
| NCC-JS124 | B | m | 2 |
| NCC-JS76.1 | B | s | 4 |
| NCC-JS77.2' | B | pp | 0 |
| NCC-JS83.2 | B | m | 1 |
| NCC-JS86 | B | m | 1 |
| NCC-JS76.2' | K | m | 28 |
| NCC-JS12 | K | s | 29 |
| NCC-JS152 | K | s | 14 |
| NCC-JS66 | K | m | 33 |
| NCC-JS102.1 | K | s | 0 |
| NCC-JS140.2 | K | s | 2 |
| NCC-JS146.2 | K | m | 36 |
| NCC-JS61.2 | B | m | 3 |
| NCC-JS114.3 | B | s | n.t. |
| NCC-JS94.1 | K | m | n.t. |
| NCC-JS98 | K | s | n.t. |
| NCC-JS 122.1 | K | g, t | n.t. |

Note:
First column, NRC code number of the isolated phage; second column, provides information on the E. coli strain on which the phage was propagated (K: non-pathogenic K12; B: pathogenic O127:K63), third column, patient identification by an NRC code (names, sex, age, patient identification number from Dhaka are available, but are not provided for confidentiality reasons); fourth column, a, acute and c, convalescent stool sample; fifth column, plaque size: g, great, m, medium, s, small, pp, pinpoint, t, turbid in contrast to clear plaques; sixth column, number of strains infected as assessed by the spot test from the 50 E. coli strains tested.

A number of phages isolated from distinct patients were closely related with respect to host range (e.g. isolates NCC-JS.4, NCC.JS.146.1 and NCC-JS66 infected up to 35 cells with a maximum difference of 4 cells; isolates NCC-JS76.2' and NCC-JS12 showing only 4 differences). However, phages with identical host range were only found in those phages having a very restricted host range (isolates NCC-JS83.1, NCC-JS89, NCC-JS114.2, NCC-JS83.2 and NCC-JS86 infecting only strains AD-24304 and O127:K63).

Lytic Potential of the Isolated Phages

Cell lysis was assessed visually as lack of turbidity in the tube incubated with the E. coli strain and the phage. The test was read when the uninfected E. coli strain had reached maximal turbidity. For example, phage isolates NCC-JS4, NCC-JS 146.1, NCC-JS66 and NCC-JS146.2 which showed in the spot test a broad and very similar host range on the pathogenic E. coli strains, differed significantly in their capacity to lyse the strains (Table 5). Phage NCC-JS4 lysed 13 out of the 50 tested E. coli cells, while phages NCC-JSI46.1, NCC-JS66 and NCC-JS146.2 lysed only 4 to 5 E. coli strains which were a subgroup of the strains lysed by phage NCC-JS 10.

TABLE 5

Lysis of the indicated pathogenic E. coli strains in broth culture by the stool phages (NCC-JS codes) with the broadest host range in the spot test.

| E. coli | Phages JS | | | | | | | | Lysis |
|---|---|---|---|---|---|---|---|---|---|
|  | 4 | D.1 | 146.1 | 66 | 146.2 | L.6 | 94.1 | 122.1 |  |
| ETEC LT+/ST+ |  |  |  |  |  |  |  |  | 0 |
| ETEC LT+/ST+ |  |  |  |  |  |  |  |  | 0 |
| ETEC LT+/ST− | + |  |  |  |  |  |  |  | 1 |
| ETEC LT+/ST− |  |  |  |  |  |  |  |  | 0 |
| ETEC LT+/ST− |  |  |  |  |  |  |  |  | 0 |
| ETEC LT+/ST+ |  |  |  |  |  |  |  |  | 0 |
| ETEC LT+/ST+ |  |  |  |  |  |  |  |  | 0 |
| ETEC LT+/ST− | + |  | + | + | + |  |  |  | 4 |
| ETEC LT+/ST− |  |  |  |  |  |  |  |  | 0 |
| ETEC LT+/ST− |  | + |  |  |  | + |  |  | 2 |
| EPEC: A/E+ | + |  |  |  |  |  | (+) |  | 2 |
| EPEC: A/E+ | + |  |  |  |  |  |  |  | 1 |
| EPEC: A/E+ | + |  |  |  |  | + |  |  | 2 |
| EPEC: A/E+ |  |  |  |  |  |  |  |  | 0 |
| EPEC: A/E+ |  |  |  |  |  |  |  |  | 0 |
| ETEC LT+/ST+; CFA1 |  |  |  |  |  |  |  |  | 0 |
| ETEC LT−/ST+; CS4; CS6 |  |  |  |  |  |  |  |  | 0 |
| ETEC LT−/ST+; CS6 |  |  |  |  |  |  |  |  | 0 |
| ETEC LT−/ST+; PCF O166 |  |  |  |  |  |  |  |  | 0 |
| ETEC LT+/ST+; CS1; CS3 |  |  |  |  |  |  |  |  | 0 |
| ETEC LT−/ST+; CFA1 |  | + |  |  |  |  |  |  | 1 |
| ETEC LT−/ST+; CS4; CS6 |  |  |  |  |  |  |  |  | 0 |
| ETEC LT+/ST+; CS1; CS3 |  | + |  |  |  | (+) |  |  | 2 |
| ETEC LT+/ST+; CS5; CS6 |  |  |  |  |  |  |  |  | 0 |
| ETEC LT+/ST+; CS5; CS6 |  |  |  |  |  |  |  |  | 0 |

TABLE 5-continued

Lysis of the indicated pathogenic *E. coli* strains in broth culture by the stool phages (NCC-JS codes) with the broadest host range in the spot test.

| E. coli | 4 | D.1 | 146.1 | 66 | 146.2 | L.6 | 94.1 | 122.1 | Lysis |
|---|---|---|---|---|---|---|---|---|---|
| EPEC |  | (+) |  |  |  |  | + |  | 2 |
| EPEC |  | (+) |  |  |  |  |  |  | 1 |
| EPEC |  |  |  |  |  |  |  |  | 0 |
| ETEC O6:H16 | + |  |  |  |  |  |  |  | 1 |
| ETEC O8:H9 |  |  |  |  |  | + |  |  | 1 |
| ETEC O15:H11 |  |  |  |  |  |  |  |  | 0 |
| ETEC O25:H42 |  |  | + | + | + |  |  |  | 4 |
| ETEC O78:H12 |  |  |  |  |  |  |  |  | 0 |
| ETEC O115:H51 |  |  |  |  |  |  |  | (+) | 1 |
| ETEC O20:H11 |  |  |  |  |  |  |  |  | 0 |
| ETEC O27:H7 |  |  |  |  |  |  |  |  | 0 |
| ETEC O128:H18 |  |  |  |  |  |  |  |  | 0 |
| ETEC O63:H− |  |  |  |  |  |  |  |  | 0 |
| ETEC O148:H28 | + |  |  |  |  |  |  |  | 1 |
| ETEC O153:H12 |  |  |  |  |  |  |  |  | 0 |
| EPEC O18:K77 | + |  |  |  |  |  |  |  | 1 |
| EPEC O20:K84 | + |  | + | + | + |  | + |  | 5 |
| EPEC O26:K60 | + |  |  |  |  |  |  |  | 1 |
| EPEC O55:K59 | + |  | + | + | + | + |  |  | 5 |
| EPEC O86:K61 |  |  |  |  |  |  |  |  | 0 |
| EPEC O111:K58 |  |  |  |  |  |  | + |  | 1 |
| EPEC O112:K66 | + |  | + | + |  |  |  |  | 3 |
| EPEC O119:K69 |  |  |  |  |  |  |  | + | 1 |
| EPEC O124:K72 | + |  |  |  |  |  |  |  | 1 |
| EPEC O125:K70 |  |  |  |  |  |  |  |  | 0 |

Note:
In the first column, the NRC *E. coli* isolates are given with their NRC codes (see Tables 3 and 2, respectively, for further information on the strains).
Columns 2-9: "+" and "(+)" means lysis and partial lysis, respectively, of the *E. coli* strain indicated in the corresponding row by the phage of the indicated column.
Column 10: number of different phage isolates lysing the indicated *E. coli* strain (total number of phages tested: 8).

The growth of uninfected and phage-infected K-12 cells was followed by OD readings (FIG. 1). Two distinct types of OD developments were observed. In the first type, the infected cells followed the OD development of uninfected cells until about 70 to 90 minutes post infection. This phase was followed by a decline of OD in the infected cells and background OD was reached at about 150 minutes post infection. In a second type of infection, demonstrated by the majority of phages the phage-infected cells showed a much earlier deviation from the OD development of the uninfected control cell. The decline to background levels was observed at about 190 min post infection (FIG. 1).

Purification of the Phages

One liter volumes of K-12 cultures were inoculated with six different phages yielding phage titers between $6 \times 10^7$ and $10^{10}$ plaque forming units (pfu)/ml. The phages from the lysate were precipitated with polyethylenglycol and the resulting phage pellet was further purified by CsCl density gradient centrifugation. The phage bands localized in the CsCl gradient were recovered and dialyzed to free them from the salt solution.

The following Table documents the efficiency of the phage purification procedure as monitored by the amount of the recovery of viral infectivity. The highest starting titers of phage infectivity were observed with phage NCC-JSI0, however this phage was also the most difficult to purify. Phage recovery ranged only from 0.3 to 5% of the starting infective material. For the other phages—at least 10% recovery was !be rule and the recovery could be as high as 40% of the initial infectivity in the crude lysate.

TABLE 6

Recovery of T4-like phages after polyethyleneglycol precipitation (pEG) and dialysis after CsCl density gradient centrifugation (CsCl).

| Phage | Lysate | PEG | CsCl |
|---|---|---|---|
| NCC-JS146.1 (1) | $6 \times 10^{10}$ | $3 \times 10^9$ (5%) | $1.8 \times 10^{10}$ (30%) |
| NCC-JS146.1 (2) | $6 \times 10^{10}$ | $2 \times 10^9$ (3%) | $9 \times 10^9$ (15%) |
| NCC-JS114.3 (1) | $1 \times 10^{12}$ | $6 \times 10^{11}$ (60%) | $4 \times 10^{11}$ (40%) |
| NCC-JS114.3 (2) | $1 \times 10^{12}$ | $4 \times 10^{11}$ (40%) | $2 \times 10^{11}$ (20%) |
| NCC-JS94.1 (1) | $4 \times 10^{11}$ | $3 \times 10^{10}$ (8%) | $6 \times 10^{10}$ (15%) |
| NCC-JS94.1 (2) | $4 \times 10^{11}$ | $2 \times 10^{10}$ (5%) | $3 \times 10^{10}$ (8%) |
| NCC-JS4 (1) | $1 \times 10^{13}$ | $2 \times 10^{11}$ (2%) | $8 \times 10^9$ (0.8%) |
| NCC-JS4 (2) | $1 \times 10^{13}$ | $1 \times 10^{11}$ (1%) | $3 \times 10^9$ (0.3%) |
| NCC-JS4 (3) | $1 \times 10^{11}$ | $2 \times 10^9$ (2%) | $5 \times 10^9$ (5%) |

Note: the first column identifies the phage isolate, the results of independent experiments are differentiated by the number in parentheses, the second column indicates the total amount of phage in 1 L of cell lysate as expressed in plaque forming units, the third column provides the total amount of plaque forming units in the PEG pellet with the percent recovery with respect to the amount in the lysate in the parentheses, the fourth column provides the total amount of plaque forming units in the dialyzed phage band isolated from the CsCl density gradient with the percent recovery with respect to the amount in the lysate in the parenthesis.

Example 2

Characterization of Phages with a 170-kb Genome Size

Material and Methods
Pulse Field Electrophoresis (pFGE)

PFGE blocks of 1% agarose containing 106 plaque-forming units of the indicated phage were incubated overnight in a lysis buffer (0.05M EDTA, 10 mM Tris pH 8.0, 1% SDS and 50 µg of proteinase K) and washed three times for one hour in 10 ml of TE (10 mM Tris pH 8.0, 1 mM EDTA). These blocks were analyzed by electrophoresis in 1% agarose low melting gel (0.5% TBE: 45 mM Tris-borate, 1 mM EDTA) for 20 hours at 6V/cm, 14° C. with a pulse time of 1-20 sec. The gel was stained for 30 min. with ethidium bromide (0.5 µg/ml).

DNA Purification

Purified phages were treated with proteinase K at a final concentration of 1 mg/ml for 2 h at 37° C. and 3 M sodium acetate pH 4.3 was added. DNA was extracted twice by phenol-chloroform and precipitated with 2 volumes of ethanol. After centrifugation, pellets were washed with 70% ethanol and resuspended in 50 µl of TE. DNA was digested with restriction enzymes according to the indications provided by the manufacturer.

Electron Microscopy

A drop of the phages suspension was applied to formvar-carbon coated copper grids for 5 min, the suspension was removed with a pipette and immediately replaced by a mixture of solutions A and B (A: 2% ammonium molybdate at pH 7.0, B: 7.5 mg bacitracine in distilled water). After 1 min the liquid was removed with filter paper. The grids were examined in a Philips CM12 transmission electron microscope at 80 kV (magnification: 176'000× or 224'000×).

Results

Twelve stool samples from different patients that showed phages with a 170-kb genome were selected for further characterization. We investigated the morphology of these phages by electron microscopy and all of them were Myoviridae with long contractile tails. The close morphological similarity with the well-known coliphage T4 is obvious. For example the elongated head measured about 110 nm by 75 nm. A collar separated the head from the tail sheath. The tail sheath by an annular substructure measured about 95 nm in length and 18 nm in width. The tail is terminated by a baseplate structure to which both short tail spikes and long tail fibers are attached. The tail fibers are about 150 nm long and are kinked at a knee joint approximately in the middle of the fiber. Phages with a 40 nm contracted tail sheath were observed. In these phages, the internal tail tube now extends beyond the contracted tail sheath. Different negative staining procedures selectively revealed various morphological features of these phages. For example, the annular structure of the tail sheath and its structural changes after tail contraction was best visualized by uranyl acetate staining, whereas the tail fibers were better seen with phosphotungstic acid negative contrast. Occasionally, whiskers could be seen at the collar.

DNA-based techniques were used to differentiate the T4-like phages isolated in the current survey. T4 phage contains glucosylated hydroxymethyl cytosine instead of cytosine. This modification makes T4 DNA resistant to digestion with most restriction enzymes. Only a few enzymes are known to cut T4 DNA (EcoRV, NdeI, Pac, SwaI, SspI, and SphI). However, from nine T4-like phage isolates selected from different patients, none was digested by EcoRV, NdeI, SwaI or SphI, and only two were digested by SspI, while all were at least partially cut by PacI.

In the next step, we probed the PacI-digested phage DNA on Southern blots with labeled T4 DNA. Some isolates showed extensive cross-hybridization with the T4 probe, while others showed weaker cross-hybridization or lacked DNA homology with T4 at the high stringency hybridization conditions.

These Southern hybridizations were confirmed by PCR using a primer pair (FR60 and FR61) from the T4 gene 32 sequence that are diagnostic (Repoila et al 1994 genomic polymorphism in the T-even bacteriophages, EMBO J 13:4181-4192) for the T-even subgroup of the T4-type phage. Phages that cross-hybridized with T4 DNA on the blots gave a clearly positive PCR result in this assay, while phage isolates that did not cross-hybridize with T4 gave no, or weak PCR bands. The phage isolates negative for PCR product for gene 32 were then retested with a PCR assay based on a set of primers (primer Mzial and caps8) in T4 gene 23 sequence which allows the detection of the pseudo T-even and schizo T-even subgroups of the T4-type phage as well as the T-evens (Tetard et al 2001, Phylogeny of the major head and tail genes of the wide-ranging T4-type bacteriophages. J. Bacteriol. 183 (1): 358-366. All but two phage isolates yielded the diagnostic g23 amplification product (Table 7). The exceptions were the stool isolate JS98 and the Swiss sewage isolate JSL.3. Both phages showed a rather conventional T4-like morphology in electron microscopy. In Southern blots JSL.3 cross-hybridized strongly with another Swiss sewage isolate JSL.5, but only weakly with a few other phages, including T4. JSL.5 cross-reacted weakly with a number of isolates, but notably not with T4.

TABLE 7

Summary of the gene 32 and gene 23 diagnostic PCR assays

| Phages | No (%) | Diagnosis |
|---|---|---|
| total no of phages tested | 47 (100) | |
| no positive in gene 32 PCR | 24 (51) | T-even phages |
| no negative in gene 32, but positive in gene 23 PCR | 21 (45) | Pseudo and Schizo T-evens |
| no negative in both gene 32 and 23 PCR | 2 (4) | morphology of T4, genetically more distant relatives |

Example 3

In-Vivo Experiments with Phages According to the Invention

Material and Methods
Experimental animals:

Eight-week-old C3H male mice (in groups of 5, otherwise noted) were used for infection experiments. Each mouse was kept in a cage with a filtered-top. The drinking water used was sterile Vittel®. Feces were taken once a day and resuspend in one ml PBS (phosphate-buffered saline). To enumerate *E. coli*, decimal dilutions of the resuspended feces were plated on Drigalski agar (Biorad). Phages were added to the drinking water. 0.5 ml of resuspended feces was filtered and phages were enumerated. Mice were sacrificed when phages were still present in the water and an autopsy was performed. Different organs were taken (colon, duodenum, ileum, jejunum, lymph nodes and liver) and tested for the presence of *E. coli* and phages.

In Vivo Phage Mix Activity in a Mouse Model:

In the first two weeks, normal water was used then sterile Vittel®.1 n the third week, a mix of four T4-like phages (JS94.1, JSD.1, JS4 and JSL.6) was added to the drinking water at a final concentration of 103 plaque forming units (pfu)/ml in the first two days then $10^5$ pfu/ml until the end of the week. In the fourth week sterile Vittel® water was given. Phages were added a second time to the water at a final concentration of $10^5$ pfu/ml, then sterile water was given, then finally $10^7$ pfu/ml phages. Phages were monitored all along the trial.

Dose Response Effect of the Phages

As previously, the same phages were given alternatively with water, four mice were used each one receiving a single concentration of phages. The first mice received phages at a final concentration of $10^3$ pfu/ml, the second had the concentration of $10^4$ pfu/ml, and the third received $10^5$ pfu/ml and the last $10^6$ pfu/ml phages. Phages were monitored all along the trial.

Phage Infection Using Axenic Mice

Eight-week-old C3H axenic male mice were used. Sterile Vittel® was used all along the trial as the drinking water. Four mice were used. Two of them were force-fed with E. coli K12 (0.5 ml at a concentration of 108 cfu/ml). Feces were taken once a day and E. coli cells were enumerated on Drigalski plates. One week after, phages were given at a concentration of $10^5$ pfu/ml. Feces were recovered four times a day. Dilutions of the resuspended feces were plated on Drigalski and after filtration, phages were enumerated. Three days later water was given and in the beginning of the next week, a second force-feeding was performed with E. coli ECOR5. Phages were given in the same conditions and the resuspended feces were treated as previously.

Results

In a first step, the E. coli normal flora was investigated. Normal water was given to five mice for two weeks then sterile Vittel® was used. Feces were recovered every day and after resuspension, E. coli cells were counted in a selective media. In conventional mice we found that the normal flora of E. coli vary from $10^5$ to $10^7$ cfu/g (FIG. 3). The average shown with the black line is linear ($R^2$=0.0002) and is of $10^6$ cfu/g which is in agreement with the results obtained by Poulsen et al. (1994, Spatial distribution of Escherichia coli in the mouse large intestine inferred from rRNA in situ hybridization. Infect. Immun. 62(11): 5191-5194). After two weeks, a mix of T4-like phages was given diluted directly in the drinking water. For a couple of days a concentration of $10^3$ pfu/ml was added to the water and phages were recovered from the feces at a concentration of $10^3$ pfu/g showing that phages could survive through the intestinal tract. The E. coli normal flora is not affected by the presence of phages. Even if the concentration is raised to 105 pfu/ml for a week, E. coli is still around $10^6$ cfu/g and phages recovered from the feces are between $10^5$ to $10^6$ pfu/g. When only sterile Vittel® water was given, no more phages were recovered from the feces. The same observations were made when phages were given twice again to mice at a final concentration of $10^5$ pfu/ml and $10^7$ pfu/ml (respectively). The amount of phage recovered from the feces is proportional to the phage received showing that few or no amplification of the phages occurs within the mouse intestine. As soon as the mouse drank pure water, no phage could have been recovered from the feces. E. coli normal flora remained unchanged, meaning that the presence of phages in the intestine did not affect the flora. An autopsy has been performed when phages were present in the intestine and the results are shown in FIG. 4B. Different organs were collected. Phages were found mainly in the colon and the duodenum while no phages were found in the lymph nodes or the liver. This suggests that phages do not go through the blood system. E. coli is present in very low levels in conventional mice, since only a couple of cells were observed in the colon and the ileum.

Lytic Activity in Axenic Mice

The infectiosity of the phages has been tested in an axenic mouse model. Two eight-week-old C3H axenic male mice were colonized with E. coli K12. A level of $10^8$ cfu/g was obtained which is more than in conventional mice but normal for axenic mice (Poulsen et aL). When adding phages in the drinking water at a concentration of $10^5$ pfu/ml, within half a day, phages were recovered in the feces at a really high concentration showing that phages lysed K-12 in the intestine and multiplied. Within this half a day, the level of E. coli dropped dramatically. One day later, phages were still at a high level but E. coli could still survive and maintained at a concentration of $10^5$ cfu/g. Even if the phages were removed from water they were still present in the feces and a decline of two logs have been observed within 3 days.

After a force-feeding with ECOR5, which is an E. coli isolated from human normal flora, mice were colonized again at a high level of E. coli (about $10^{10}$ cfu/g). ECOR5 is not affected by phage J894.1 already used in this test, and for this reason, colonization was quick and stable. Even if phages were again added to the drinking water, cell count remained the same whereas phage titer reached the concentration given to the mice in the water.

When phages were not any longer present in the intestine, an autopsy was performed and results are shown in FIG. 4A. E. coli seems to colonies mainly the colon and the small part of the intestine. Phage titer was also determined and no phage was found (data not shown) in any organ tested.

Different Phages Survives the Gut-Intestine

Alternatively, sterile Vittel® water was given a week and phages at a final concentration of $10^7$ pfu/ml were given the next week. Four different phages were tested (JS4, JSD.1, JSL.6 and JS94.1 respectively). Four mice were treated with phages and the last mouse was kept as a control and received only sterile-Vittel® water. Phages were monitored all along the trial.

In this experiment, we have given to five mice the T4-like phages composing the mix of the previous trial one by one. All phages reacted in the same manner. Phages were added to the water and a day after they were recovered in the feces at the same concentration as given. When phages were removed from the water, no more phages were found in the feces after 24 hours. Whatever the phage used in the drinking water, the same results are obtained.

If four different concentrations of these phages are given to four different mice, a dose response effect can be noticed. When a very low concentration ($10^3$ pfu/ml) is used, phages are present in the feces but not in a stable manner. When increasing this concentration with one log, phages were present in the feces all along the treatment and recovered at a higher level. With one and two more logs the same observations were done.

Example 4

Dry Pet Food

A feed mixture is made up of about 58% by weight of corn, about 5.5% by weight of corn gluten, about 22% by weight of chicken meal, 2.5% dried chicory, $10^6$ pfu/ml bacteriophage cocktail, salts, vitamins and minerals making up the remainder. The fed mixture is fed into a preconditioner and moistened. The moistened feed is then fed into an extruder-cooker and gelatinized. The gelatinized matrix leaving the extruder is forced through a die and extruded. The extrudate is cut into pieces suitable for feeding to dogs, dried at about 110° C. for about 20 minutes, and cooled to form pellets.

This dry dog food is able to prevent or to treat infectious disorders caused by pathogenic Enterobacteriaceae such as E. coli or Salmonella infections, such as gastroenteritis, diarrheal or urinary diseases in pets.

Example 5

Nutritional Formula

A nutritional composition is prepared, and which contains for 100 g of powder: 15% of protein hydrolysate, 25% of fats, 55% carbohydrates (including maltodextrin 37%, starch 6%, sucrose 12%), traces of vitamins and oligoelements to meet daily requirements, 2% minerals and 3% moisture and $10^6$ pfu/ml bacteriophage cocktail 13 g of this powder is mixed in 100 ml of water. The obtained formula is particularly intended for preventing gastroenteritis, diarrhea or urinary diseases in humans.

What is claimed is:

1. A phage preparation comprising a broad host range isolated phage selected from the Myoviridae family having a genome size of 170 kb and lytic activity against pathogenic *E. coli* or *Salmonella* strains, wherein the isolated phage is virulent and safe to administer to a human or animal, wherein the isolated phage is an obligate virulent phage with a contractile tail, and wherein the isolated phage is incorporated into a product selected from the group consisting of a food product, a pharmaceutical product, a nutritional supplement and a composition for oral administration, wherein the isolated phage is selected from the group consisting of NCC-JS4 (CNCM I-2763), NCC-JS35 (CNCM I-2764), NCC-JS1.4 (CNCM I-2765), and NCC-JSF (CNCM I-2766).

2. The phage preparation of claim 1, wherein the isolated phage has a head that is elongated measuring about 110 nm by 75 nm and a collar separating the head from a tail sheath.

3. The phage preparation of claim 2, wherein the isolated phage has an annular substructure measuring about 95 nm in length and 18 nm in width and a tail that is terminated by a baseplate structure having both short tail spikes and long tail fibers.

4. The phage preparation of claim 2, wherein the isolated phage has tail fibers that are about 150 nm long and are kinked at a knee joint approximately in the middle of the fiber.

5. The phage preparation of claim 1, wherein the genome is not digestable by EcoRV, NdeI, SwaI, or SphI, and digestable by PacI.

6. The phage preparation of claim 1, wherein the phage preparation comprises at least two isolated Myoviridae phages.

7. The phage preparation of claim 1, wherein the food product is a pet food.

8. The pet food of claim 7, comprising up to 58% by weight corn, approximately 5.5% by weight of corn gluten, about 22% by weight of chicken meal, and at least $10^6$ pfu/ml the isolated phage.

9. The phage preparation of claim 1, wherein the phage isolate is in an amount of at least $1.10^4$ pfu (plaque forming unit)/ml.

10. The phage preparation of claim 1, further comprising a prebiotic or a probiotic micro-organism.

11. The phage preparation of claim 1, wherein the isolated phage is isolated and amplified on a non-pathogenic strain of *E. coli*.

12. The phage preparation of claim 11, wherein the non-pathogenic *E. coli* strain is K-12.

* * * * *